United States Patent [19]

Ford et al.

[11] 4,256,957
[45] Mar. 17, 1981

[54] BOTTLE INSPECTION APPARATUS

[75] Inventors: Geoffrey E. Ford; Antis N. Pantelides, both of Bedford, England

[73] Assignee: T I Fords Limited, Kempston, England

[21] Appl. No.: 930,167

[22] Filed: Aug. 2, 1978

[30] Foreign Application Priority Data

Aug. 11, 1977 [GB] United Kingdom ............... 33820/77

[51] Int. Cl.³ ............................................. H01J 39/12
[52] U.S. Cl. ................................. 250/223 B; 209/524
[58] Field of Search ................... 250/223 B; 209/524, 209/526; 356/260

[56] References Cited
U.S. PATENT DOCUMENTS 3,727,068  4/1973  Poynton et al. ............. 250/223 B X
3,770,969  11/1973  Ansevin et al. ................. 250/223 B Primary Examiner—David C. Nelms
Assistant Examiner—Darwin R. Hostetter
Attorney, Agent, or Firm—Brisebois & Kruger

[57] ABSTRACT

The invention relates to a bottle inspection apparatus wherein an image of an area, such as the base, of the bottle to be inspected is projected on to an integrated circuit device comprising an array of photodiodes arranged in a plurality of rows in combination with means to interrogate each diode in turn, along each row in turn, to provide a video signal comprising a sequence of electrical signals corresponding to the light energy each diode has received, and wherein the video signal is differentiated and means are provided for gating-out unwanted signals outside the area of the bottle to be inspected whereby to generate a differentiated video output signal representative of dirt or foreign bodies in the bottle.

8 Claims, 17 Drawing Figures

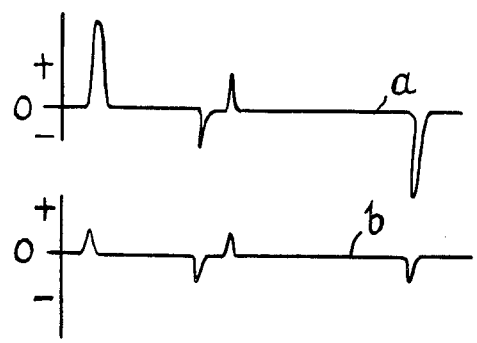
Fig. 2
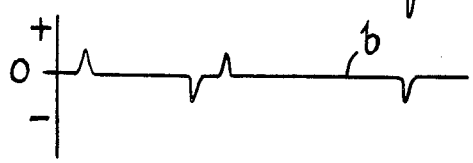
Fig. 3a
Fig. 3b
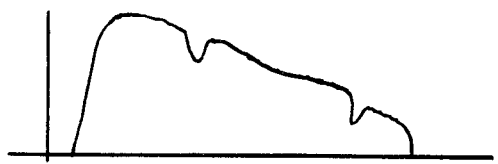
Fig. 4
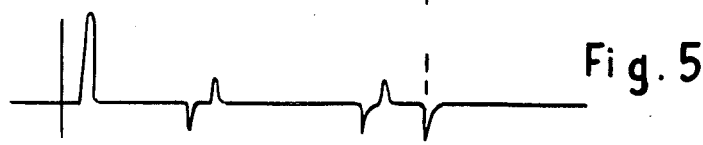
Fig. 5
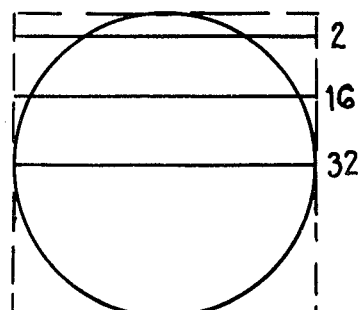
Fig. 6 line 1. 2. 3. 4.　　　62 63 64
← 1 frame → ← next frame

← 1 frame →

↓ direction of scan

BOTTLE INSPECTION APPARATUS

FIELD OF THE INVENTION

The present invention relates to apparatus, herein referred to as bottle inspection apparatus, for the detection of dirt or foreign bodies in transparent bottles or other containers (herein referred as "bottles") before they are filled and offered for sale, particularly in bottles such as milk or beer bottles which are re-used after washing. Examples of such machines are disclosed in U.S. Pat. Nos. 3,727,068, 3,746,165 and 3,411,009.

SUMMARY OF THE INVENTION

Such inspection on a high speed bottling line must be carried out whilst the bottle is moving through the inspection station at normal speed, and if foreign bodies are to be detected the permissible movement whilst scanning the whole area, e.g. the base area, to be inspected must be limited to approximately 1 mm. to avoid blur to the image. This requires that the whole area must be scanned in about 1 millisecond.

The present invention has for its object to provide an inspection arrangement which meets this requirement and which is also capable of inspecting clear and coloured bottles over a wide range of light transmission percentages.

The present invention consists in a bottle inspection apparatus wherein an image of an area, such as the base, of the bottle to be inspected is projected on to an integrated circuit device comprising an array of photo-diodes arranged in a plurality of rows in combination with means to interrogate each diode in turn, along each row in turn, to provide a video signal comprising a sequence of electrical signals corresponding to the light energy each diode has received, and wherein the video signal is differentiated and means are provided for gating-out unwanted signals outside the area of the bottle to be inspected whereby to generate a differentiated video output signal representative of dirt or foreign bodies in the bottle.

The integrated circuit device may comprise 64 rows each of 64 photo-diodes, that is 4096 photo-diodes in all, arranged in a square array. Such a device is capable of being scanned in one millisecond and has sufficient resolution to detect a 1 mm. foreign body in a typical beverage bottle.

The proportion of incident light transmitted through a glass bottle varies widely from sample to sample, depending on the thickness of the glass and its colour, e.g. amber or green. However, usable video signals can be obtained from the photo-diode array when inspecting both light and dark coloured bottles provided the ratio of their respective light transmission percentages is not greater than about 7:1. By differentiating the video signal an output is obtained which is proportional to the rate of change of the signals and is, for practical purposes, independent of the light transmission factor of the glass bottle.

According to a feature of the invention, a differentiated frame video signal representative of the outputs of successive whole rows of diodes is also produced, and after unwanted signals at the beginning and end of a frame are gated out, generates, if one or more complete rows of photo-diodes is/are obscured by a foreign body, a reject signal to divert the contaminated bottle from the bottle conveyor. Without this further signal a foreign body which obscures a whole row or rows of diodes would not be detected.

According to a further feature of the invention, the differentiated signal pulses are converted to constant amplitude pulses having time durations corresponding to the length of time the differentiated input pulse amplitude is above a preset threshold. The time duration of the constant amplitude pulses may be variable and by providing an arrangement which only gives an output when the signal pulse duration exceeds a preset pulse length, pulses of shorter duration than the preset value may be eliminated from the output controlling the reject apparatus. Thereby the sensitivity of the system may be adjusted to avoid rejecting bottles which are clean but have minor flaws.

In order that the invention may be more clearly understood reference will now be made to the accompanying drawings.

BRIEF DESCRIPTION OF THE DRAWINGS

FIGS. 2 to 16 are waveform and other diagrams for explaining the operation of the apparatus of FIG. 1.

DETAILED DESCRIPTION OF THE INVENTION

Figure 1:
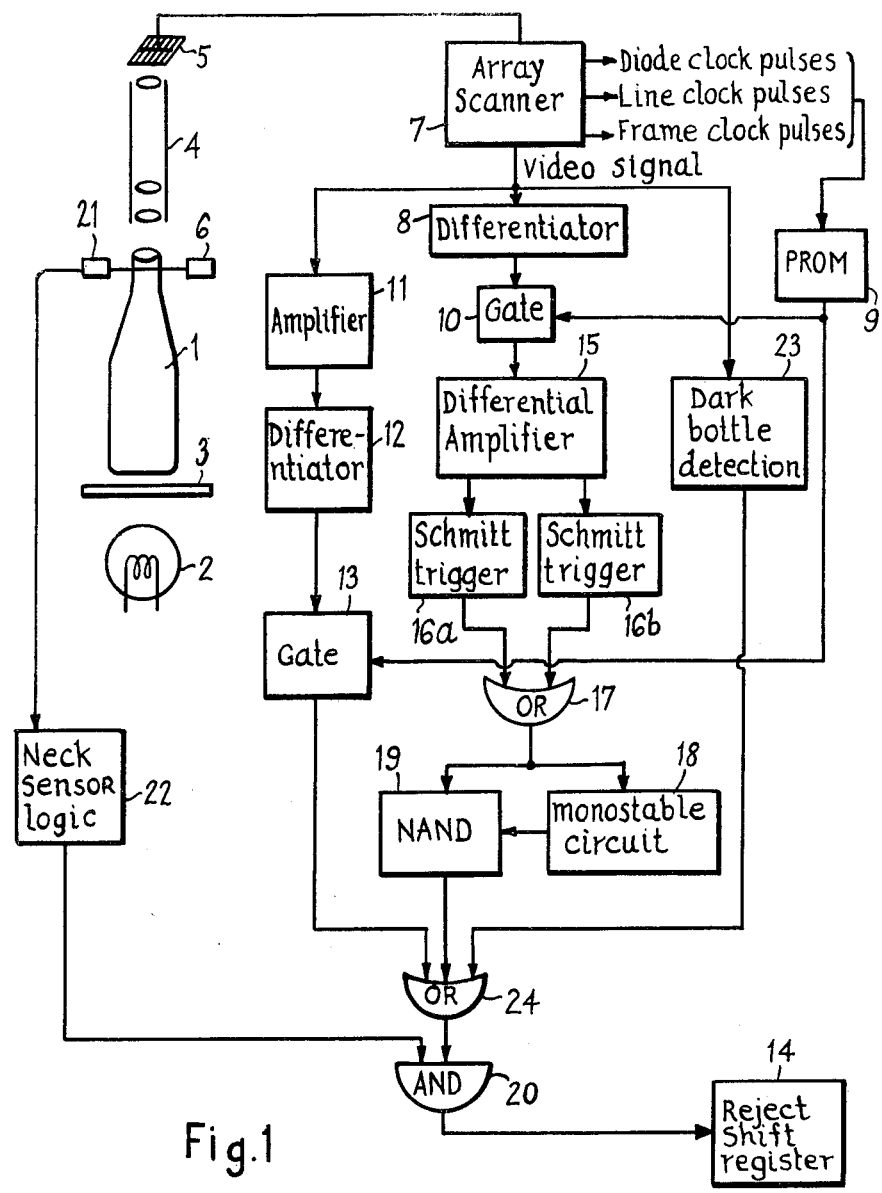
FIG. 1 is a schematic diagram of a bottle inspection apparatus according to one embodiment of this invention.

In the embodiment shown in FIG. 1, the base of a bottle 1, when it is in the inspection station, is illuminated from below by means of a lamp 2 and a rotatable diffusing screen 3 as described in U.S. Pat. No. 3,727,068. A lens system 4 mounted vertically above the bottle projects an image of the circular base of the bottle onto an integrated circuit device 5 comprising a square array of photo-diodes and associated logic circuits. A suitable integrated circuit device having 64 rows each of 64 photo-diodes and known as "2DI 64×64 matrix array" is made by Integrated Photomatrix Limited of Dorchester, England.

The lens system magnification is chosen so that the image diameter is as large as can be contained within the square array. Different bottle diameters and heights can be accommodated by raising or lowering the whole inspection head which consists of the lens system 4, scanned array 5 and a bottle position sensor 6 to be described later, and also by adjusting the relative spacing of the individual elements of the lens system 4 to obtain the correct magnification and focus. In this way the final bottle image on the array can be made the same size irrespective of the diameter and height of the bottle being inspected.

The photo-diode array 5 is scanned by an array scanner 7 to provide a video signal. As already mentioned, the proportion of incident light transmitted through the base of a bottle varies widely depending on the thickness of glass and its colour. FIG. 2 shows in curve a the video signal from a single line of diodes across the diameter of the bottle image for a light coloured bottle containing an opaque foreign body; curve b is a similar video signal for a dark bottle. By passing the video signal through a differentiating circuit 8, differentiated signals proportional to the rate of change of amplitude of the video signal resulting from a foreign body are derived, as shown in FIGS. 3a and 3b, which are substantially independent of the different light transmissions of different bottles. In FIGS. 3a and 3b a dark to light transition is shown as a positive polarity signal and a light to dark transition as a negative polarity signal.

The glass distribution in the base of a bottle is often non-uniform with one side much thicker than the other, wherefore much less light is transmitted through the thick side compared with the thin side. Differentiation of the video signal also overcomes this difficulty. FIG. 4 shows the video signal from such a bottle and FIG. 5 the differentiated result. In this case two foreign bodies are shown and the one on the dark side of the base gives a similar signal to that on the light side after differentiation, whilst the relatively slow rate of change due to the thickness variation can be ignored.

The video signal from a whole frame will consist of a sequence of 64 line signals each representing the signals generated by the 64 photo-diodes in a row, but only a portion of each line signal will contain information relevant to a circular bottle. FIG. 6 shows the bottle image on the array and it can be seen that only on the central line, No. 32, is the whole line signal required, whilst above and below this a decreasing proportion of the total line signal contains the required information. For example, line No. 2 intersects the bottle near its circumference and only the central 12 diodes in the line contain bottle information. On either side of this, unwanted signals may be present, for example as shown in FIGS. 3a and 3b where there is an unwanted signal at the beginning and end of each line.

The image of some bottle bases is surrounded by a dark ring due to refraction of the light in the region where the cylindrical body joins the base of the bottle. This will also cause unwanted signals to be generated in portions of each line outside the area of interest.

The clock pulses of the array scanner 7 used to interrogate the array, diode by diode along a line, and line by line over the whole frame of the array, are also used to address a programmable read only memory (PROM) 9 and this latter can be programmed to generate a gating pulse of the correct length for each line so that after gating the video signal in the gate 10, the only pulses that remain in the differentiated video output are those due to foreign bodies in the bottle, i.e. those within the circular area shown in FIG. 6.

The PROM may be programmed to define an area of any shape within which desired signals may occur and outside which spurious signals must be rejected. For example, triangular or eliptical bottles could be inspected by appropriate programming.

Figure 7:
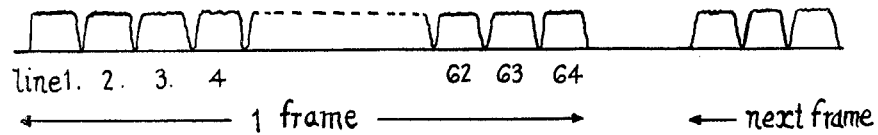
Figure 8:
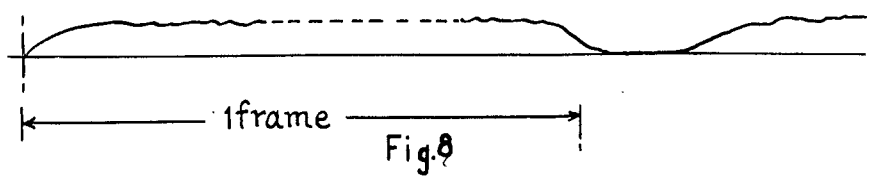

A large foreign body having straight edges aligned parallel to the lines scanned will not be detected because it would obscure all the active diodes in the line and, since there would be no change in illumination along the line, the differentiated output would be zero. To overcome this problem, a reject signal is also derived from the video signal comprising a whole frame which, before differentiating and gating, consists of 64 line signals as shown in FIG. 7. This signal is passed to an amplifier 11 having a restricted high frequency response so that the output cannot follow the fast change taking place between each line signal and a smoothed output results for each frame as shown in FIG. 8.

Figure 9:
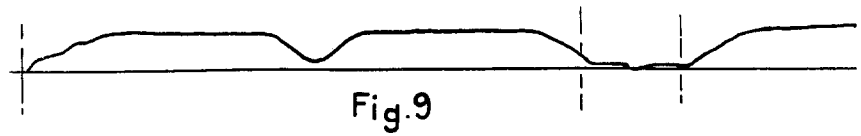
Figure 10:
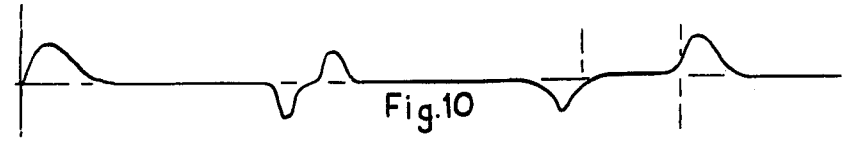

A large straight object totally obscuring one or more lines will give a signal as shown in FIG. 9, which after differentiating in a differentiating circuit 12 provides an output as shown in FIG. 10.

Figure 11:
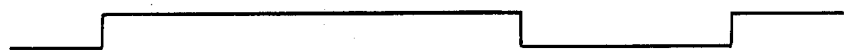

The two unwanted signals at the beginning and end of each frame may be gated out with a pulse as shown in FIG. 11 generated in the PROM 9 and applied to a gating circuit 13 so that only the wanted signal remains and can be used together with any foreign body pulses on the line signals to send a reject pulse to the reject shift register 14 which operates some mechanism such as that described in co-pending patent application Ser. No. 873,683, now U.S. Pat. No. 4,158,624 issued June 19, 1979, to divert the contaminated bottle from the bottle conveyor.

Figure 12:
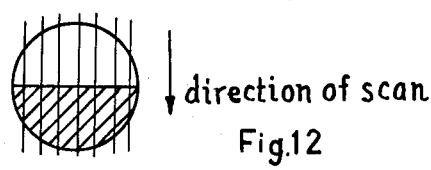

The two differentiators 8 and 12, one dealing with line signals and the other with the complete frame signal, both give outputs of either polarity depending on whether the illumination change is light to dark or viceversa. With a small object both polarities will be present but a large object obscuring say half the base may generate signals of only one polarity depending on the direction of scan across the edge of the object. FIG. 12 shows half the base obscured and with the direction of scan shown there will only be light to dark transitions on each line and therefore only negative going pulses.

It is convenient at some stage in the signal processing to invert signals of one polarity so that they are all the same. The differentiated signals obtained from foreign bodies in the bottle are pulses, approximately triangular in shape, but varying in amplitude and duration depending on the size and opacity of the body detected. A very small body which only obscures one diode in a line will be small in amplitude and of short duration compared with a body which obscures say ten consecutive diodes; the difference being illustrated at d and D respectively in FIG. 13.

The differentiated signals may be used to drive a "Schmitt" trigger giving a constant amplitude output pulse for the length of time the input is above a preset threshold. This latter may be set to a low value so that even the signal from a single obscured diode will give an output from the trigger.

Figure 13:
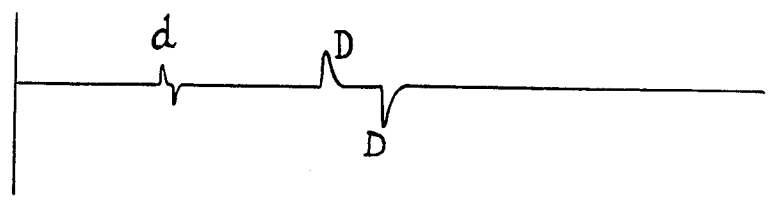

Separate "Schmitt" triggers 16a, 16b may be used on the positive and negative polarity parts of the signal shown in FIG. 13 which are amplified in the differential amplifier 15. The resulting pulses of the same polarity are combined in the "OR" gate 17. The result of this operation on the signal of FIG. 13 is shown in FIG. 14.

Figure 14:
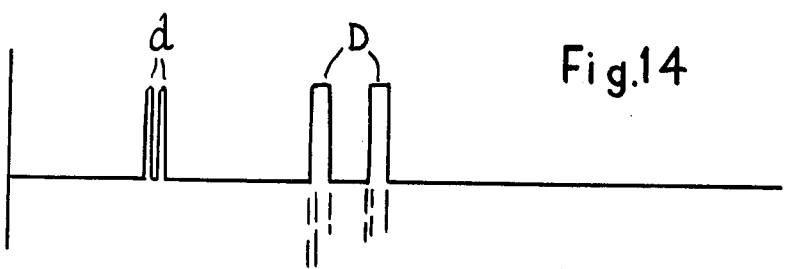
Figure 15:
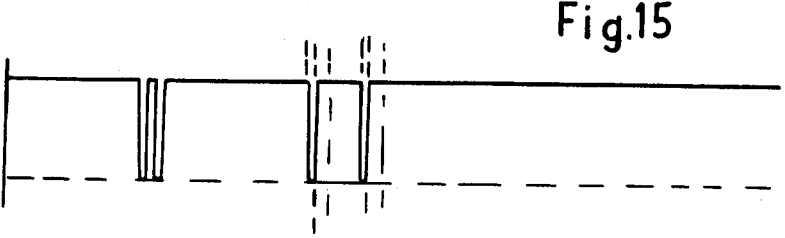

The pulse train of FIG. 14 provides the input to a monostable circuit 18 and also to a NAND gate 19. The monostable circuit 18 is made to give an output pulse of constant amplitude and time duration for each input pulse, the time duration being adjustable by altering the time constant of the Resistance-Capacitance coupling components. The output from the monostable circuit 18, which is shown in FIG. 15, provides a second input to the NAND gate 19.

Figure 16:
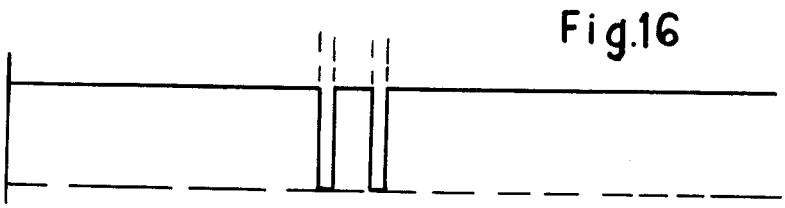

The NAND gate 19 will now only give an output when the signal pulse duration exceeds the preset pulse length of the monostable circuit 18. Thus the circuit performs as a pulse length comparitor and, by adjusting the time constant of the monostable circuit 18, all pulses of shorter duration than the preset pulse length may be eliminated from the NAND gate output which is fed to the reject shift register 14. FIG. 16 shows the output of the NAND gate when the monostable circuit is adjusted to eliminate short duration signals such as that shown at d for a small body in FIGS. 13 and 14.

Thus, very small objects obscuring one diode can be detected or ignored by adjusting the time constant of the monostable circuit appropriately. Also a permanent spurious signal caused by the failure of one diode in the array may be ignored. The arrangement also gives a measure of immunity from very short duration interference pulses which may have been picked up by the earlier parts of the circuit.

In a practical bottle inspection machine it is necessary to be able to vary the sensitivity to different sized objects to avoid rejecting too many clean bottles with minor glass flaws or bottles carrying conveyor lubricant foam on the outside.

With the system described, the sensitivity may be varied as described or by adjusting the time constant of the differentiators or by varying the threshold at which the "Schmitt" triggers operate.

The diode array is continuously being scanned and delivers the video signal, which is processed in the manner described above. An AND gate 20 is provided in the output and is operated by a bottle position sensor 6 so that reject signals, if any, are only obtained when a bottle is in the inspection station.

The sensor is arranged to allow a bottle movement of 1 to 2 mm. before switching the output gate off. Any reject signals obtained during this time are used to eject the contaminated bottle or to feed a memory so that the bottle rejection may take place subsequently, as described in the aforesaid patent application Ser. No. 873,683, now U.S. Pat. No. 4,158,624 issued June 19, 1979.

The preferred method of sensing the bottle position employs 2 or 3 narrow beams of infra red or visible light positioned so that they are interrupted by the mouth of a bottle passing through the inspection station. The spacing of the two outer beams in relation to the mouth diameter determines the distance the bottle travels during inspection. The photo-transistors (only one is shown at 21) which receive the two or three beams provide signals which operate logic devices 22 to perform other functions as well as that of gating the signals to the reject device, for example, they can be used to gauge the mouth diameter so that oversize or undersized bottles may be rejected. Furthermore, logic may be provided so that inspection is only initiated when the bottle passes through the beams in the correct direction. This eliminates problems caused by a bottle moving backwards a short distance following impact with a neighbouring bottle.

Other detection systems can be incorporated with this inspection system and their respective reject signals can be fed into the system so that the same reject mechanism may be used for a number of purposes. For example, a sensor may be provided to detect water in the bottle being inspected. Also a dark bottle detector 23 controlled by the video signal or by a separate single photo-transistor arranged to view the whole base area through the bottle mouth, may be provided to reject a bottle with a totally obscured base or with a cork jammed in its neck. The output from the dark bottle detector 23 may be combined in the "OR" gate 24 with the outputs from the NAND gate 19 and from the gate 13.

In an alternative arrangement the output from the gate 13 may be fed into the differential amplifier 15.

A machine which has been constructed incorporating the inspection system described above has been found to be capable of inspecting coloured bottles having light transmissions of from 7 to 50% at speeds in excess of 800 per minute, and of detecting small objects down to 1 mm. size, including small chips of broken glass.

We claim:

1. A bottle inspection apparatus for detecting dirt or foreign bodies in transparent bottles while being conveyed to bottle filling apparatus, comprising means for moving bottles to be inspected past inspection means, said inspection means comprising a source of illumination, diffuser means between said source and a bottle being inspected whereby diffusely to illuminate an area of the bottle to be inspected, means for projecting an image of said area on to an integrated circuit device comprising an array of photodiodes arranged in a plurality of rows with a plurality of diodes in each row in combination with array scanner means cyclically to scan the array and interrogate each diode in turn, along each row in turn, to provide a video signal comprising a sequence of electrical signals corresponding to the light energy each diode has received, means synchronised with said array scanner to generate gating pulses of the desired length for each row, and means feeding said video signal to electric circuit means including means for differentiating said video signal and gate means controlled by said gating pulses for gating-out unwanted signals outside the said area of the bottle to be inspected whereby to generate differentiated signal pulses representative of dirt or foreign bodies in the bottles.

2. A bottle inspection apparatus as claimed in claim 1, wherein said electric circuit means includes means producing a differentiated frame video signal representative of the video signal comprising a whole frame consisting of all the successive whole rows of diodes, and means synchronised with said array scanner for gating-out unwanted signals at the beginning and end of said differentiated frame video signal whereby to generate a differentiated signal pulse if a complete row of photodiodes is obscured by dirt or a foreign body.

3. A bottle inspection apparatus as claimed in claim 1, wherein the electric circuit means includes means for inverting differentiated signal pulses of one polarity so that all signal pulses are of the same polarity.

4. A bottle inspection apparatus as claimed in claim 3, wherein the electric circuit means includes means for converting the differentiated signal pulses to constant amplitude pulses having a time duration corresponding to the length of time the differentiated pulse amplitude is above a preset threshold.

5. A bottle inspection apparatus as claimed in claim 4, and including means for varying said preset threshold.

6. A bottle inspection apparatus as claimed in claim 4, and including means for suppressing constant amplitude pulses having a time duration less than a predetermined value.

7. A bottle inspection apparatus as claimed in claim 1 and including a bottle position sensor and the electric circuit means includes a shift register and means enabling any signal pulses representative of the presence of dirt or a foreign body in a bottle to be passed to said shift register only when a bottle is in a position where it can be inspected.

8. A bottle inspection apparatus as claimed in claim 1, wherein the interrogation of the photo-diodes of the integrated circuit device is controlled by clock pulses which are also used to address a programmable read only memory which is programmed to generate gating pulses of the desired length for each row, means feeding said video signal to a first differentiator, to a dark bottle detector and to an amplifier having a restricted high frequency response so that its output cannot follow the fast change in the video signal between the interrogation of successive rows of diodes, a first gate connected to the output of said first differentiator and controlled by said gating pulses to effect said gating-out of unwanted signals outside said area of the bottle to be inspected, the output from said first gate being fed to a differential amplifier the positive and negative outputs from which are fed to two "Schmitt" triggers respectively each producing a constant amplitude output pulse of the same polarity for the length of time the differentiated input pulse is above a preset threshold, a first "OR" gate combining the output pulses of said two "Schmitt" triggers and delivering the output pulses to a monostable circuit producing an output pulse of constant amplitude and time duration for each input pulse and also to a "NAND" gate, means for adjusting the time duration of the output pulses of said monostable circuit, means connecting the monostable circuit output to provide a second input to said "NAND" gate, a second differentiator connected to the output from said amplifier having a restricted high frequency response and having its differentiated output pulses fed to a second gate controlled by said gating pulses to effect gating-out of unwanted signals at the beginning and end of each output pulse corresponding to the interrogation of a whole frame consisting of all the successive whole rows of diodes, means connecting the outputs of said second gate, said "NAND" gate and said dark bottle detector to a second "OR" gate, a bottle position sensor for sensing when a bottle is in a position where it can be inspected, means connecting the outputs from said bottle position sensor and said second "OR" gate to an "AND" gate, and bottle reject control means connected to respond to the output from said "AND" gate.

* * * * *